(12) United States Patent
Swenson et al.

(10) Patent No.: US 7,056,531 B1
(45) Date of Patent: Jun. 6, 2006

(54) SUSTAINED RELEASE COMPOSITIONS FOR ORALLY ADMINISTERED SUBSTANCES AND METHODS

(75) Inventors: Andy Swenson, Payson, UT (US); James Wagstaff, Orem, UT (US)

(73) Assignee: Nature's Way Products, Inc., Springville, UT (US)

( * ) Notice: Subject to any disclaimer, the term of this patent is extended or adjusted under 35 U.S.C. 154(b) by 0 days.

(21) Appl. No.: 09/849,611

(22) Filed: May 4, 2001

Related U.S. Application Data (60) Provisional application No. 60/201,815, filed on May 4, 2000.

(51) Int. Cl.
*A61K 9/20* (2006.01)
*A61K 9/22* (2006.01)

(52) U.S. Cl. .................. 424/465; 424/464; 424/468

(58) Field of Classification Search ............... 424/464, 424/465, 468, 489, 474, 475, 476, 477
See application file for complete search history.

(56) References Cited

U.S. PATENT DOCUMENTS

| | | | | |
|---|---|---|---|---|
| 4,159,345 A * | 6/1979 | Takeo et al. | .................. | 514/781 |
| 4,643,894 A | 2/1987 | Porter et al. | .................. | 424/35 |
| 4,684,516 A * | 8/1987 | Bhutani | .................. | 424/469 |
| 4,725,441 A | 2/1988 | Porter et al. | .................. | 424/479 |
| 4,828,841 A | 5/1989 | Porter et al. | .................. | 424/479 |
| 4,994,276 A | 2/1991 | Baichwal et al. | .................. | 424/440 |
| 5,128,143 A * | 7/1992 | Baichwal et al. | .................. | 424/464 |
| 5,135,757 A | 8/1992 | Baichwal et al. | .................. | 424/465 |
| 5,455,046 A | 10/1995 | Baichwal | .................. | 424/457 |
| 5,470,581 A * | 11/1995 | Grillo et al. | .................. | 424/479 |
| 5,480,479 A | 1/1996 | Signorino | .................. | 106/162 |
| 5,534,263 A | 7/1996 | Wong et al. | .................. | 424/473 |
| 5,571,334 A * | 11/1996 | Dunn et al. | .................. | 127/70 |
| 5,662,933 A | 9/1997 | Baichwal et al. | .................. | 424/457 |
| 5,667,804 A | 9/1997 | Wong et al. | .................. | 424/472 |
| 5,807,580 A | 9/1998 | Luber | .................. | 424/480 |
| 5,958,456 A | 9/1999 | Baichwal et al. | .................. | 424/489 |
| 5,972,999 A * | 10/1999 | Murad | .................. | 514/474 |
| 6,020,000 A | 2/2000 | Wong et al. | .................. | 424/472 |
| 6,030,645 A | 2/2000 | Tritsch et al. | .................. | 424/490 |
| 6,069,172 A * | 5/2000 | Bertini et al. | .................. | 514/570 |
| 6,120,803 A * | 9/2000 | Wong et al. | .................. | 424/473 |
| 6,346,519 B1 * | 2/2002 | Petrus | .................. | 514/62 |
| 6,417,227 B1 * | 7/2002 | Lord et al. | .................. | 514/529 |
| 6,627,749 B1 * | 9/2003 | Kumar | .................. | 536/56 |
| 2002/0012701 A1 * | 1/2002 | Kolter et al. | .................. | 424/468 |
| 2003/0100611 A1 * | 5/2003 | Berner et al. | .................. | 514/561 |
| 2004/0053887 A1 * | 3/2004 | Obae et al. | .................. | 514/57 |

OTHER PUBLICATIONS

Grain Processing Corporation, Maltrin® Maltodextrins and Corn Syrup Solids, http://www.grainporcessing.com/food/malinfo.html, Apr. 23, 2000.*

(Continued)

*Primary Examiner*—Susan Tran
(74) *Attorney, Agent, or Firm*—Workman Nydegger (57) ABSTRACT

Sustained release composition for orally administered active substances that comprises maltodextrin and cellulose. This composition is suitable for forming tablets, gels when exposed to the fluids in the gastric environment, and provides an effective sustained release medium for glucosamine-based compounds. This composition is effectively used as a stomach guard.

37 Claims, 3 Drawing Sheets

OTHER PUBLICATIONS

"*The Simultaneous Determination of Muramic Acid and Glucosamine in Soil by High-Performance Liquid Chromatography*," Biology and Fertility of Soils, vol. 6, No. 2, 125-30 (1988).

Gaines Nutrition Online Health Food Services, Beta Carotene (Dry) Product Information, http://www.gaines.com/html/NaturesW/NW640info.html, available on Internet by at least Apr. 23, 2000.

Gaines Nutrition Online Health Food Services, Niacin Product Information, http://www.gaines.com/html/NaturesW/NW640info.html, available on Internet by at least Apr. 23, 2000.

Gaines Nutrition Online Health Food Services, Pantothenic Acid Product Information, http://www.gaines.com/html/NaturesW/NW642info.html, available on Internet by at least Apr. 23, 2000.

Gaines Nutrition Online Health Food Services, Vitamin B1 Product Information, http://www.gaines.com/html/NaturesW/NW631info.html, available on Internet by at least Apr. 23, 2000.

Gaines Nutrition Online Health Food Services, Vitamin B2 Product Information, http://www.gaines.com/html/NaturesW/NW632info.html, available on Internet by at least Apr. 23, 2000.

Gaines Nutrition Online Health Food Services, Zinc Product Information, http://www.gaines.com/html/NaturesW/NW682info.html, available on Internet by at least Apr. 23, 2000.

Healthy-Sunshine.com Ginkgo Biloba, Time-Release, http://www.healthy-sunshine.com/ginkgo_tr.htm, available on Internet by at least Apr. 23, 2000.

Healthy-Sunshine.com, Flash-Ease, http://www.healthy-sunshine.com/flash-ease.htm, avalable on Internet by at least Apr. 23, 2000.

HealthIQ, IQToolkit(tm) Glossary, Definition for Maltodextrin, http://www.healthiq.com/HealthcareResources/Glossary/G394.htm, available on Internet by at least Apr. 23, 2000.

Phys:Maltodextrin, http://www.phys.com/b_nutrition/03encyclopedia/02terms/m/maltodex.html, available on Internet by at least Apr. 23, 2000.

Phys:Maltodextrin, http://www.phys.com/b_nutrition/03encyclopedia/02terms/additive.html, available on Internet by at least Apr. 23, 2000.

Phys:Generally Recognized as Safe, http://www.phys.com/b_nutrition/03encyclopedia/02terms/g/gras.html, available on Internet by at least Apr. 23, 2000.

Grain Processing Corporation, Maltrin® Maltodextrins and Corn Syrup Solids, http://www.grainprocessing.com/food.malinfo.html, available on Internet by at least Apr. 23, 2000.

Matsutani Chemical Product: Maltodextrin, http://www.matsutani.com/maltodextrinmain.html, available on Internet by at least Apr. 23, 2000.

Corn Usage, Maltodextrins (Food Uses), http://204.240.36.10/com/usage/malto.htm, available on Internet by at least Apr. 23, 2000.

Paradise Chiropractic BPU, Inc., http://www.paradisebpu.com/metagenics-ultra.html, available on Internet by at least Apr. 23, 2000.

NU'RISH Chocolate Malt, http://www.inforarea.com/vitamins/Nu-rish_from-Lametco.htm, available on Internet by at least Apr. 23, 2000.

\* cited by examiner

SUSTAINED RELEASE COMPOSITIONS FOR ORALLY ADMINISTERED SUBSTANCES AND METHODS

CROSS-REFERENCE TO RELATED APPLICATIONS

This application claims priority to U.S. Provisional patent application Ser. No. 60/201,815, filed on May 04, 2000, which application is incorporated herein by specific reference.

BACKGROUND OF THE INVENTION

1. The Field of the Invention

The present invention relates generally to sustained release compositions. More specifically, the present invention relates to sustained release gelling compositions that help to prevent adverse side effects of orally administered substances such as medicines and dietary supplements.

2. The Relevant Technology

Substances such as medicines and dietary supplements can cause undesirable side effects after they are ingested. In particular, the oral administration of these substances can cause undesirable gastrointestinal side effects that range from slight discomfort to actual damage of the wall tissues in digestive system organs. Because of such detrimental side effects, some individuals have to discontinue the intake of a preparation that is prescribed or recommended for beneficial purposes.

These undesirable side effects can be caused by the direct action of the ingested substance on the gastrointestinal wall or by indirect damage that is in turn caused by the breakdown products and/or reaction products of the ingested substance with digestive system substances. In any case, it is desirable to prevent such detrimental side effects so that they do not diminish the beneficial action of the ingested substance.

It is also desirable to provide an excipient that is suitable for tableting and whose constituents are readily available biocompatible substances. It is further desirable to provide an excipient that is effective for sustained release of a variety of active substances that are typically taken, orally, and whose detrimental side effects are derived from any one of a variety of causes, such as direct contact with digestive system walls, break-down products, and reaction products with digestive system substances.

BRIEF SUMMARY OF THE INVENTION

The present invention has been developed in response to the present state of the art and, in particular, in response to problems and needs that have not been solved heretofore.

It is an object of the present invention to provide compositions for oral administration of substances including dietary supplements and medicines such that the detrimental side effects of these substances are minimized or even eliminated.

It is another object of the present invention to provide sustained release compositions that are biocompatible and that include tableting properties such as those of flow agents, binders and gelling agents.

It is another object of the present invention to provide sustained release compositions that are effective in reducing or even eliminating the detrimental side effects derived from some substances that are taken as medicines or as supplements, including effects derived from the direct contact of the ingested substance with digestive system walls, the effects of break-down products, and the effects of reaction products with digestive system substances.

To achieve the foregoing objects, and in accordance with the invention as embodied and broadly described herein, compositions according to the present invention comprise combinations of maltodextrin and cellulose. The cellulose is preferably used in the form of powdered cellulose, and its combination with maltodextrin provides gelling effects and it slows the disintegration of the tablet, thus contributing to the sustained release of the medicine or supplement in the tablet. In addition, the gelling effects prevent the direct contact with the stomach wall of a substantial amount of the porosity irritant medicine or supplement.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to illustrations of the appended drawings. Understanding that these drawings refer only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention is directed to sustained release compositions that slow the disintegration of the delivery specimen, such as a tablet, a capsule, a pill, and other similar delivery specimens, and that form a gel upon oral ingestion. In one embodiment of this invention, a composition is provided in the form of a stomach guard for the oral administration of glucosamine and active preparations that contain glucosamine.

Active substances such as medicines and dietary supplements which are administered orally can damage the digestive system, and in particular the lining of the stomach. For example, it has been reported that glucosamine can be a stomach irritant in certain individuals, and it is thought that the irritation occurs when glucosamine contacts the stomach lining.

Glucosamine, and other preparations that contain glucosamine, are typically administered in the form of capsules and tablets. It is believed that after these capsules and tablets are ingested they irritate the stomach lining. The irritation could be due to any one among a variety of mechanisms and/or combination of mechanisms. For example, the capsule skin itself dissolves very quickly and leads to stomach irritation because of the sudden release of the glucosamine. Similarly, the sudden dissolution of the tablets followed by the exposure of the stomach lining to the released glucosamine could cause stomach lining irritation. According to another mechanism, an ingested tablet could become in contact with the stomach wall and dissolve at or near the contact site, thus producing a relative large concentration of glucosamine in situ that could cause local stomach lining irritation. Other mechanisms might involve the sudden appearance within the stomach of products derived from the break down or reaction of glucosamine with substances in the gastric fluids.

The specific and detailed mechanism whereby an orally administered active substance such as a medicine or a supplement can irritate the stomach lining is unknown for most of such substances, including glucosamine. Nevertheless, irritation mechanisms that depend on the fast release into the stomach of the active substance contained in a tablet should be significantly off-set if the active substance is released slowly. A slow and sustained release has in this regard a variety of beneficial effects. For example, the stomach medium is not suddenly exposed to a sharp increase in the concentration of the active substance. In addition, an ingested tablet is not suddenly dissolved in its entirety at any given spot, and consequently does not give rise to any locally high concentration of the active substance. Furthermore, any irritant reaction product or irritant by-product of the active substance that could form in the stomach does not reach undesirably high concentrations if the active substance is released slowly within that medium.

Despite the possible variety of irritant mechanisms and the complexity of such mechanisms, it has been found in the context of the present invention that a composition that includes maltodextrin and cellulose in certain amounts is a sustained release composition. This composition has also been found to be a suitable composition for tableting. Further, this composition is capable of forming a protective gel in the gastric environment. Likewise, it has been discovered that this composition acts as a stomach guard protecting the stomach lining from possible detrimental side effects of active substances such as glucosamine. These findings are viewed as an unexpected result in light of teachings provided by conventional references. These teachings concern film coated tablet compositions that have enhanced disintegration properties. The film coatings comprise mixtures of substances that include maltodextrin and cellulose derivatives, such as hydroxypropyl methylcellulose, methylcellulose, ethylcellulose, and hydroxypropyl cellulose. See, e.g., U.S. Pat. No. 5,807,580, col. 2, ll. 11–15, patent which is herein incorporated by reference in its entirety. These film coatings are reportedly used for coating a variety of medicaments where a quick onset of action is desirable, with the coated tablet or caplet exhibiting enhanced disintegration characteristics in gastric acid when compared to conventional film-coated tablets or caplets. See, id., col. 3, ll. 7–9, 44–47. These effects are precisely opposite to those sought as an objective in the present invention.

Maltodextrin has been defined as a nonfermentable sugar that is obtained by controlled depolymerization of cornstarch. Maltodextrin has been generally used as a texturizer and bulking agent in foods and as flow agent and binder in tablet formulations. Although a variety of maltodextrin grades can be used in embodiments of the present invention, a preferred maltodextrin is a MALTRIN® maltodextrin whose grade is M510. It will be appreciated by one skilled in the art that various other grades of maltodextrin are available and may be used in the present invention instead of the M510 maltodextrin, including by way of example but not limitation, grades M580 and M700. Although other types of maltodextrin could be used in alternate embodiments of this invention, MALTRI® maltodextrins are preferred because they reportedly contain no proteins from wheat, barley, oats or rye, and thus are reported safe for individuals with celiac disease. In addition to these nonallergenic properties, the preferred form and grade of maltodextrin has the preferred properties for tableting purposes.

Cellulose in embodiments of the present invention is preferably used in the form of powdered cellulose. This grade of cellulose is typically used in encapsulation formulations, but it not generally used in tablet formulations because it does not flow or compress well. Cellulose used in preferred embodiments of this invention is marketed with the product designation ELCEMA EXP 9250 by Degussa AG. Degussa-Hüls Corp. This product's specifications include a degree of polymerization from about 440 to about 2250 and a pH in the range from about 5.0 to about 7.5. Embodiments of the present invention have used this cellulose with a reported degree of polymerization of about 1432, a reported pH of about 6.7, and a reported density of about 0.176 g/ml. Reported particle size as air jet particle size includes a large fraction of particles above 32 µm, about 17.5% above 63 µm, and about 0.4% above 125 µm.

Maltodextrin and powdered cellulose can be combined in wide ranges in embodiments of the present invention. Preferred compositions according to the present invention are such that the tablet includes cellulose in a weight percentage from about 5% to about 13%. Other embodiments of this invention comprise cellulose in a weight percentage of at least about 4% up to about 14%. As customary, percentages provided hereinbelow refer to weight percentages unless it is explicitly specified otherwise. Furthermore, weight percentages are provided with reference to the total gross tablet weight, unless specified otherwise.

Preferred embodiments of this invention contain an amount of maltodextrin that is in excess of the amount of cellulose. Weight ratios referred to the binary combination only to these two constituents expressed as (amount of cellulose):(amount of maltodextrin) range in embodiments of the present invention from about 1:9 to about 2:3, and more preferably from about 1:4 to about 3:7.

The cellulose/maltodextrin composition of the present invention is incorporated into the active substance delivery specimen, such as a tablet, according to conventional compaction techniques, and more particularly according to conventional tableting techniques. In an embodiment of the present invention that is formed as a tablet, for example, the powdered cellulose and the maltodextrin according to the present invention form part of the tablet bulk. In addition to powdered cellulose and maltodextrin, tablets according to the present invention can contain conventional additives and coating materials.

EXAMPLES

The following examples are presented in order to more specifically teach the compositions and characteristics of sustained release preparations according to the present invention. The examples include preparations with glucosamine, with a combination of glucosamine and chondroitin sulfate, and with a combination of glucosamine and methyl sulfonyl methane (MSM). The examples also contain comparative time release data using glucosamine tablet embodiments of the present invention and five conventional glucosamine preparations.

To date, numerous tests have been performed comparing conventional release formulations to those designed using the composition of the present invention. Below are specific examples of the compositions according to the present invention and comparisons between release times for conventional preparations and release times for preparations according to the present invention. Additionally, a number of hypothetical, or "prophetic", examples have been included based on preparations which would be expected, based on experience, to possess the properties described hereinafter. The actual examples are written in the past tense, while the hypothetical examples are written in the present tense in order to distinguish between the two.

Example 1

An embodiment of the sustained release composition according to the present invention was incorporated into a glucosamine/chondroitin tablet in the form of a preparation that was obtained by mixing about 41.5% GLUCOSAMINE SUL 68/95% GRAN. KCL 30 MESH, about 24.5% CHONDROITIN SULFATE 90% GRAN. (BOVINE), about 17.7% MALTRIN M510 (GPC), about 7.3% CELLULOSE, POWDERED EXP 9250, about 5.6% UNITAB 102 FCC, about 1.6% STEARIC ACID PWD 5016 NF FG VEG, about 1.0% SYLOID 244FP PWD, about 0.1% COATING MATERIALS, about 0.4% OPADRY II CLEAR 52M19144, and about 0.4% METHYLCELL OPADRY CL YS-2-7035. When referred to the binary mixture of cellulose and maltodextrin only, the relative amounts of these two constituents in this Example were about 29.4% cellulose and about 70.6% maltodextrin, or a weight ratio of about 3:7. This preparation was effectively formed into tablet forms which exhibited sustained released as characterized below.

Example 2

An embodiment of the sustained release composition according to the present invention was incorporated into a glucosamine/MSM tablet in the form of a preparation that was obtained by mixing about 40.0% GLUCOSAMINE SUL. 68/95% GRAN. KCL 30 MESH, about 26.6% METHYL SULFONYL METHANE (MSM), about 17.2% MALTRIN M510 (GPC), about 7.1% CELLULOSE, POWDERED EXP 9250, about 4.8% UNITAB 102 FCC, about 2.3% STEARIC ACID PWD 5016 NF FG VEG, about 0.5% SYLOID 244FP PWD, about 0.1% COATING MATERIALS, about 0.7% OPADRY II CLEAR 52MP19144, and about 0.7% METHYLCELL OPADRY CL YS-2-7035. When referred to the binary mixture of cellulose and maltodextrin only, the relative amounts of these two constituents in this Example were about 29.2% cellulose and about 70.8% maltodextrin, or a weight ratio of about 3:7. This preparation was effectively formed into tablet forms which exhibited sustained released as characterized below.

Example 3

An embodiment of the sustained release composition according to the present invention was incorporated into a glucosamine tablet in the form of a preparation that was obtained by mixing about 59% GLUCOSAMINE SUL. 68/95% GRAN. KCL 30 MESH, about 24.6% MALTRIN M510 (GPC), about 6.1% CELLULOSE, POWDERED EXP 9250, about 6.6% UNITAB 102 FCC, about 1.7% STEARIC ACID PWD 5016 NF FG VEG, about 0.4% SYLOID 244FP PWD, about 0.1% COATING MATERIALS, about 0.8% OPADRY II CLEAR 52M19144, and about 0.8% METHYLCELL OPADRY CL YS-2-7035. When referred to the binary mixture of cellulose and maltodextrin only, the relative amounts of these constituents in this Example were about 19.8% cellulose and about 80.2% maltodextrin, or a weight ratio of about 1:4. This preparation was effectively formed into tablet forms which exhibited sustained released as characterized below.

Example 4

An embodiment of the sustained release composition according to the present invention was incorporated into a glucosamine tablet in the form of a preparation that was obtained by mixing about 53.6% GLUCOSAMINE HCL. 95% GRAN. 30 MESH, about 23.8% MALTRIN M510 (GPC), about 5.9% CELLULOSE, POWDERED EXP 9250, about 13.1% UNITAB 102 FCC, about 1.6% STEARIC ACID PWD 5016 NF FG VEG, about 0.4% SYLOID 244FP PWD, about 0.1% COATING MATERIALS, about 0.7% OPADRY II CLEAR 52M19144, and about 0.7% METHYLCELL OPADRY CL YS-2-7035. When referred to the binary mixture of cellulose and maltodextrin only, the relative amounts of these constituents in this Example were about 19.9% cellulose and about 80.1% maltodextrin, or a weight ratio of about 1:4. This preparation was effectively formed into tablet forms which exhibited sustained released as characterized below.

Example 5

An embodiment of the sustained release composition according to the present invention is incorporated into a glucosamine tablet in the form of a preparation that is obtained by mixing about 60.0% GLUCOSAMINE SUL. 68/95% GRAN. KCL 30 MESH, about 28.0% MALTRIN M510 (GPC), and about 12.0% CELLULOSE, POWDERED EXP 9250. When referred to the binary mixture of cellulose and maltodextrin only, the relative amounts of these constituents in this Example are about 30.0% cellulose and about 70.0% maltodextrin, or a weight ratio of about 3:7. This preparation is formed into sustained release tablets. Other embodiments of this composition are prepared with the same percentages of maltodextrin and cellulose, about 54.0% of glucosamine sulfate, and about 6.0% of additives such as coating materials and flow agents.

Example 6

An embodiment of the sustained release composition according to the present invention is incorporated into a glucosamine tablet in the form of a preparation that is obtained by mixing about 60.0% GLUCOSAMINE SUL. 68/95% GRAN. KCL 30 MESH, about 32.0% MALTRIN M510 (GPC), and about 8.0% CELLULOSE, POWDERED EXP 9250. When referred to the binary mixture of cellulose and maltodextrin only, the relative amounts of these constituents in this Example are about 20.0% cellulose and about 80.0% maltodextrin, or a weight ratio of about 1:4. This preparation is formed into sustained release tablets. Other embodiments of this composition are prepared with the same percentages of maltodextrin and cellulose, about 54.0% of glucosamine sulfate, and about 6.0% of additives such as coating materials and flow agents.

Example 7

An embodiment of the sustained release composition according to the present invention is incorporated into a glucosamine tablet in the form of a preparation that is obtained by mixing about 50.0% GLUCOSAMINE SUL. 68/95% GRAN. KCL 30 MESH, about 45.0% MALTRIN M510 (GPC), and about 5.0% CELLULOSE, POWDERED EXP 9250. When referred to the binary mixture of cellulose and maltodextrin only, the relative amounts of these constituents in this Example are about 10.0% cellulose and about 90.0% maltodextrin, or a weight ratio of about 1:9. This preparation is formed into sustained release tablets. Other embodiments of this composition are prepared with the same percentages of maltodextrin and cellulose, about 45.0% of glucosamine sulfate, and about 5.0% of additives such as coating materials and flow agents.

Example 8

An embodiment of the sustained release composition according to the present invention is incorporated into a glucosamine tablet in the form of a preparation that is obtained by mixing about 75.0% GLUCOSAMINE SUL. 68/95% GRAN. KCL 30 MESH, about 15.0% MALTRIN M510 (GPC), and about 10.0% CELLULOSE, POWDERED EXP 9250. When referred to the binary mixture of cellulose and maltodextrin only, the relative amounts of these constituents in this Example are about 40.0% cellulose and about 60.0% maltodextrin, or a weight ratio of about 2:3. This preparation is formed into sustained release tablets. Other embodiments of this composition are prepared with the same percentages of maltodextrin and cellulose, about 67.0% of glucosamine sulfate, and about 8.0% of additives such as coating materials and flow agents.

Assays and dissolution of glucosamine products were performed according to the following procedure. Glucosamine quantitation was achieved by chromophore attachment through derivatization followed by HPLC (high performance liquid chromatography) separation with UV (ultra violet) detection. This technique is based on the analytical technique described by Laszlo Zelles, *The simultaneous determination of muramic acid and glucosamine in soil by high-performance liquid chromatography*, Biology and Fertility of Soils, vol. 6, no. 2, 125–30 (1988), which is herein incorporated by reference in its entirety. Quantitation of glucosamine was performed by referring HPLC-UV analytical data for test samples to data obtained by the same technique for a standard solution.

The standard solution was prepared by dissolving commercially available glucosamine hydrochloride of 98% purity to form an aqueous solution that had a glucosamine concentration of 0.474 mg/ml (or 0.484×0.98 mg/ml glucosamine). HPLC analytical data regarding this standard solution are provided in Table 1. The terms "peak 1" and "peak 2" in the tables provided hereinbelow refer in conventional terms to the HPLC-UV peaks associated with glucosamine, and the numerical values in the corresponding columns are the areas under each one of such peaks. The term "total" in the same tables refers to the sum of the areas under peaks 1 and 2.

Glucosamine tables according to the present invention as well as conventional glucosamine tablets were dissolved according to the following procedure. One tablet for each assay was stirred in 500 ml of water at 100 rpm at 37° C. In a USP compatible dissolution apparatus, aliquots were removed at the times indicated in the time columns in the tables provided below, typically at 15 min, 30 min, 60 min, 120 min, and 180 min. These aliquots were assayed for glucosamine as described hereinabove. For each sample material according to the present invention and for each conventional sample material, the assays were performed in triplicate by running the assays as described hereinabove, independently and individually with three different tablets.

TABLE 1

| peak 1 | peak 2 | total |
|--------|--------|-------|
| 1413 | 1636 | 3049 |
| 1496 | 1648 | 3144 |
| | Average: | 3097 |

Tables 2–4 provide time release data for an embodiment of the present invention in the form of three glucosamine tablets were assayed individually with the results for tablet 1 reported in Table 2, for tablet 2 reported in Table 3, and for tablet 3 reported in Table 4. These three tablets were samples of an embodiment of the present invention that was manufactured according to the formulation provided in Example 1. The fifth column in each one of Tables 2–4 displays the amounts of glucosamine in mg that were released from each tablet at specific times. The sixth column in each one of Tables 2–4 displays the amounts of glucosamine release from each tablet as percentages at specific times. Because of manufacturing process variations, tablet 1 contained 493 mg glucosamine, tablet 2 contained 538 mg glucosamine, and tablet 3 contained 489 mg glucosamine. Based on data provided in Table 3, the amount of glucosamine released, expressed as a percentage of the glucosamine initially present in the tablet 1, has been plotted as a function of time in FIG. 1.

Tables 2–4 indicate that the active substance (glucosamine in this embodiment) in the sustained release tablets according to the present composition is released over a time period that varies from two to three hours. The same tabular data also show that the sustained release composition of the present invention permits the slow release of the active substance in a generally monotonic fashion over the release time period. Accordingly, the sustained release composition of the present invention effectively provides a release medium and release mechanism such that the active substance is gradually and continuously incorporated into the receiving environment, for example the gastric environment. This gradual and continuous incorporation is characterized in that the amount of active substance released into the receiving environment does not undergo any early sudden increase that would cause at least one sharp concentration maximum shortly after intake. Consequently, a receiving environment such as the gastric environment is not exposed to a high concentration of the active substance that would cause undesirable irritation. Furthermore, absence of exposure to high concentration of the active substance applies to the receiving environment generally and also to local sites in such environment. The absence in the receiving environment of any sharp concentration maximum of the released active substance is a quantitative aspect of the active substance sustained release pattern according to the present invention. The absence in the receiving environment of exposure to high concentration of the released active substance is a spacial distribution aspect of the active substance sustained release pattern according to the present invention. The beneficial effects of these spacial and quantitative aspects of the active substance sustained release according to the present invention are further discussed below.

The spacial distribution of the released active substance concentration in the receiving medium according to the present invention has beneficial consequences. Because the receiving medium is not generally exposed to high concentrations of the active substance, the cause of general irritation or some other form of general damaging side effect is suppressed. Because the receiving medium is not locally exposed to high concentrations of the active substance, the cause of in situ irritation or some other in situ form of damaging side effect is also suppressed.

The quantitative aspect of the released active substance concentration in the receiving medium according to the present invention has also beneficial consequences. As reasoned in the foregoing discussion, irritation or some other form of damaging side effect could be caused by any one among a variety of factors, such as a high concentration of the active substance itself, a high-concentration of break down products of the active substance, and a high concentration of reaction products of the active substance with substances present in the receiving medium. The slow release provided by the compositions of the present invention prevents the incorporation of the active substance at sudden high concentrations. Because the active substance is gradually incorporated into the receiving medium, this incorporation should also be the bottle neck for any increase in the amounts of its break down products and reaction products.

TABLE 2

| time/min | peak 1 | peak 2 | total | glucosamine/ (mg/tablet) | % glucosamine released |
|---|---|---|---|---|---|
| 15 | 973 | 1021 | 1994 | 162 | 33 |
| 30 | 1389 | 1456 | 2845 | 230 | 47 |
| 60 | 2010 | 2147 | 4157 | 337 | 68 |
| 120 | 2941 | 3143 | 6084 | 493 | 100 |

TABLE 3

| time/min | peak 1 | peak 2 | total | glucosamine/ (mg/tablet) | % glucosamine released |
|---|---|---|---|---|---|
| 15 | 942 | 997 | 1939 | 157 | 29 |
| 30 | 1285 | 1377 | 2662 | 216 | 40 |
| 60 | 2096 | 2200 | 4296 | 348 | 65 |
| 120 | 2914 | 3124 | 6038 | 489 | 91 |
| 180 | 3206 | 3440 | 6646 | 538 | 100 |

TABLE 4

| time/min | peak 1 | peak 2 | total | glucosamine/ (mg/tablet) | % glucosamine released |
|---|---|---|---|---|---|
| 15 | 786 | 814 | 1600 | 130 | 27 |
| 30 | 1233 | 1284 | 2517 | 204 | 42 |
| 60 | 1832 | 936 | 2768 | 224 | 46 |
| 120 | 2910 | 3125 | 6035 | 489 | 100 |

Tables 5–8 provide time release data for conventional glucosamine preparations. Table 5 provides analytical data for KAL glucosamine tables based on a total release of 417 mg glucosamine sulfate per tablet. Table 6 provides analytical data for Sundown glucosamine tablets based on a total release of 497 mg glucosamine hydrochloride per tablet. Table 7 provides analytical data for Source Naturals glucosamine tablets based on a total release of 530 mg glucosamine sulfate per tablet. Table 8 provides analytical data for SolGar glucosamine tablets based on a total release of 1007 mg of glucosamine sulfate per tablet. Columns 1–4 in Tables 5–8 provide quantitative data analogous to the corresponding columns in Tables 2–4. The fifth column in each one of Tables 5–8 provides the percentage of released glucosamine computed with respect to the total glucosamine found in the sample upon completion dissolution of the tablet. The sixth column in each one of Tables 5–8 provides the percentage of released glucosamine computed with respect to the total glucosamine given in the product specifications as printed on the product label.

TABLE 5

| time/min | peak 1 | peak 2 | total | % glucosamine released | % glucosamine released/label |
|---|---|---|---|---|---|
| 15 | 10.05 | 11.91 | 21.96 | 97 | 81 |
| 30 | 10.33 | 12.42 | 22.75 | 100 | 83 |
| 60 | 9.57 | 11.27 | 20.84 | 92 | 76 |

TABLE 6

| time/min | peak 1 | peak 2 | total | % glucosamine released | % glucosamine released/label |
|---|---|---|---|---|---|
| 15 | 8.67 | 10.5 | 19.17 | 67 | 66 |
| 30 | 12.54 | 15.02 | 27.56 | 96 | 96 |
| 60 | 13.2 | 15.46 | 28.66 | 100 | 99 |
| 90 | 12.94 | 15.23 | 28.17 | 98 | 98 |

TABLE 7

| time/min | peak 1 | peak 2 | total | % glucosamine released | % glucosamine released/label |
|---|---|---|---|---|---|
| 15 | 9.76 | 10.76 | 20.52 | 65 | 69 |
| 30 | 15.21 | 15.84 | 31.05 | 99 | 104 |
| 60 | 15.35 | 16.16 | 31.51 | 100 | 106 |

TABLE 8

| time/min | peak 1 | peak 2 | total | % glucosamine released | % glucosamine released/label |
|---|---|---|---|---|---|
| 10 | 1826 | 1861 | 3687 | 72 | 72 |
| 20 | 2483 | 2531 | 5014 | 97 | 98 |
| 30 | 2519 | 2576 | 5095 | 99 | 100 |
| 45 | 2521 | 2575 | 5096 | 99 | 100 |
| 60 | 2554 | 2600 | 5154 | 100 | 101 |

The percentages of released glucosamine shown in Tables 5–8 indicate that the tested conventional preparations release the substantially entire glucosamine content in less than about thirty minutes from the time in which they were exposed to the aqueous environment. Furthermore, these data show that the tested conventional glucosamine preparations release most of the glucosamine content during the initial half hour into the process of tablet dissolution.

Figure 1:
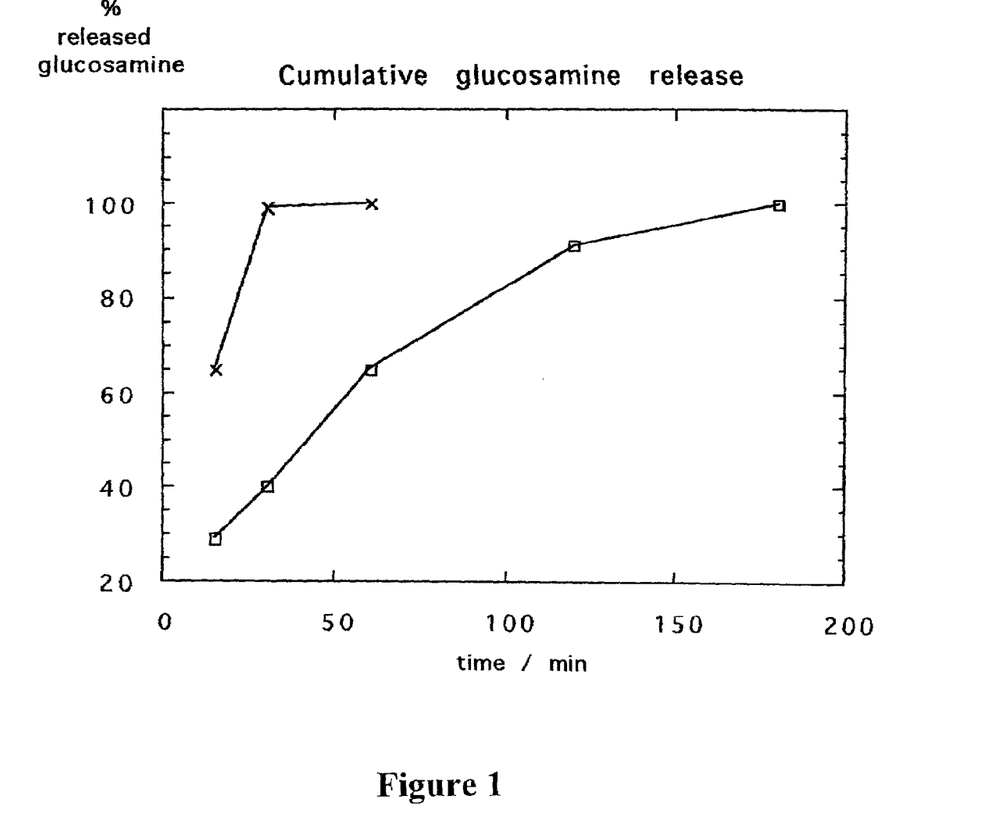
FIG. 1 shows cumulative glucosamine release as a function of time for an embodiment of the present invention (line joining squares) and for a conventional preparation (line joining crosses).

FIG. 1 shows the cumulative glucosamine release as a function of time for the embodiment of the present invention whose test data are provided in Table 3 (line joining squares in FIG. 1) and for the conventional preparation whose test data are provided in Table 7 (line joining crosses in FIG. 1). Data for these two preparations have been plotted in the same graph as shown in FIG. 1 because they have a similar glucosamine content per tablet: about 538 mg/tablet in the embodiment of the present invention and about 530 mg/tablet in the conventional preparation. The graph depicted in FIG. 1 shows that the glucosamine release from the embodiment of the present invention is generally monotonic. In other words, the percentage of released glucosamine gradually increases over time, and it takes over two hours for the entire glucosamine content to be released. In contrast, the same graph shows that the entire glucosamine content of the conventional preparation is released in significantly less than one hour, with 99% of the glucosamine being released in the initial 30 minutes. This slow and gradual release of glucosamine is also reflected by the data provided in Tables 2, 4 for other embodiments of the present invention.

Figure 2:
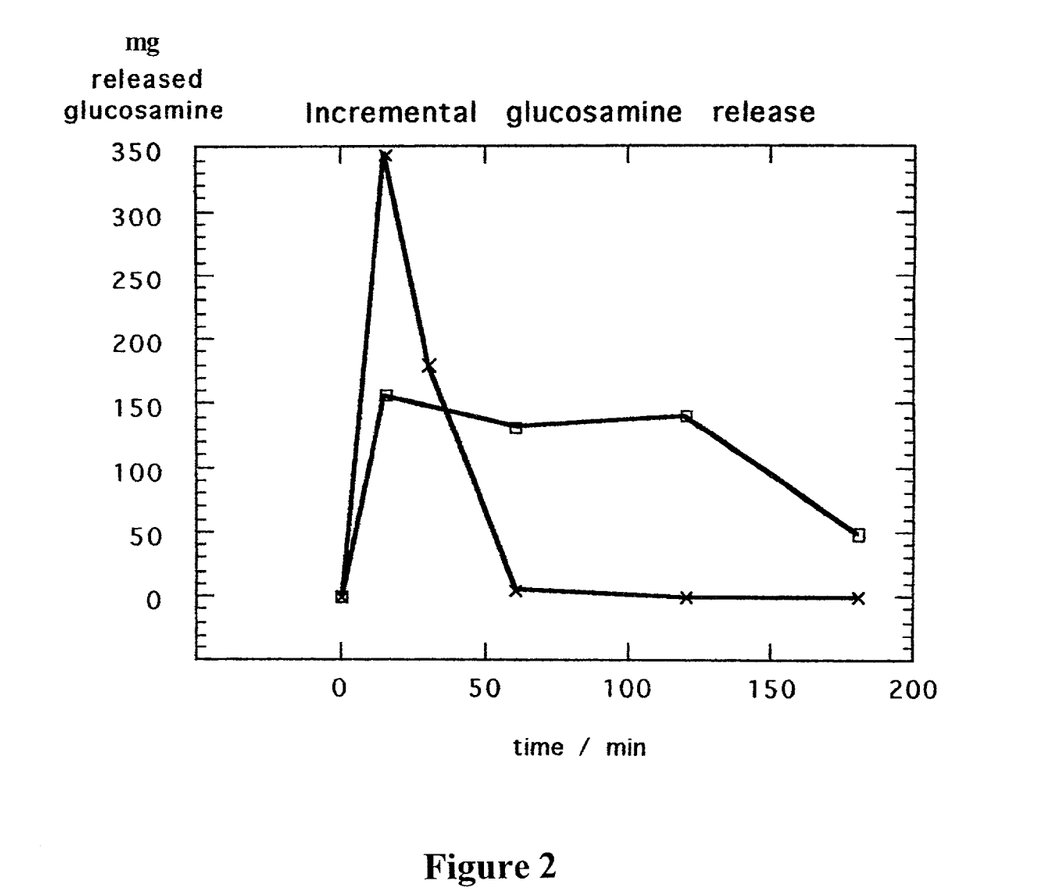
FIG. 2 shows incremental glucosamine release as a function of time for an embodiment of the present invention (line joining squares) and for a conventional preparation (line joining crosses).

FIG. 2 shows the incremented glucosamine release as a function of time for the embodiment of the present invention whose test data are provided in Table 1 (line joining squares in FIG. 2) and for the conventional preparation whose test data are provided in Table 7 (line joining crosses in FIG. 2). As indicated in reference to the FIG. 1, data for these two preparations have been plotted in the same graph as shown in FIG. 2 because they have a similar glucosamine content per tablet. The graph depicted in FIG. 2 shows that the glucosamine release from the embodiment of the present invention remains approximately constant between about 100 mg and 140 mg of glucosamine for about one-hour intervals during at least two hours. Furthermore, only about 29% of the glucosamine in the tablet, or about 157 mg glucosamine, are released during the initial 15 minutes. In contrast, the same graph shows that the glucosamine release from the conventional preparation takes place as a sharp spike, with a surge in glucosamine release that causes about 99% of the glucosamine, or about 524.7 mg glucosamine, to be released in the initial 30 minutes. This slow and gradual release of glucosamine is also reflected by the data provided in Tables 2, 4 for other embodiments of the present invention.

Figure 3:
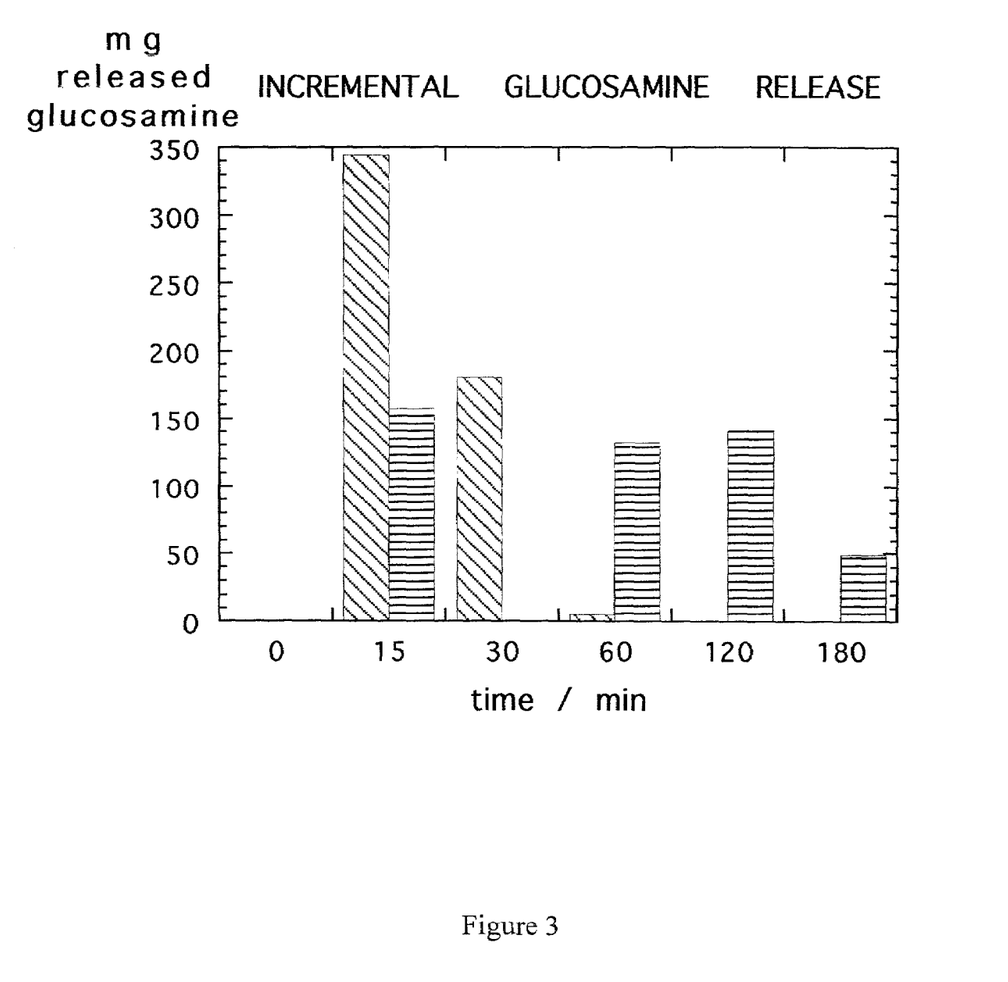
FIG. 3 shows as a bar diagram the incremental glucosamine release as a function of time for the same embodiments shown in FIG. 2, where data for this embodiment of the present invention is displayed by bars with horizontal shading segments and data for a conventional preparation is displayed by bars with inclined shading segments.

To provide another representation of the data depicted in FIG. 2, FIG. 3 shows as a bar diagram the incremental glucosamine release as a function of time for the same embodiments shown in FIG. 2, where data for this embodiment of the present invention is displayed by bars with horizontal shading segments and data for a conventional preparation is displayed by bars with inclined shading segments.

Methods for providing sustained release of a bioactive substance according to the present invention comprise the oral administration of a composition containing cellulose and maltodextrin in amounts that correspond to embodiments of the compositions according to the present invention. In an embodiment of these models, the administered composition is in the form of at least one solid specimen, and the composition is taken orally a number of times that depends on the time interval during which the bioactive substance is to be effectively present in the gastrointestinal system. This administration provides a delivered effective amount of bioactive substance according to a sustained and controlled pattern for a time period ranges from about one hour to about three hours. By way of example but not of limitation, one tablet with the cellulose and maltodextrin composition of the preparation according to the present invention that corresponds to the lines joining squares in FIGS. 1–2 is taken once every two hours for four hours. This intake provides an amount of bioactive substance in the range from about 50 mg to about 150 mg for at least four hours. Accordingly, these administration would satisfy the need for an effective amount of bioactive substance within this range for at least four hours. Additional sustained and controlled delivery patterns are envisaged according to the present invention. As shown hereinabove, establishing these additional patterns entails the determination of the sustained release, cumulative or incremented, of the bioactive substance as a function of time as shown, for example, in the discussion of FIGS. 1–2. Therefore, the effective amount of bioactive substance that is released and the time interval during which the bioactive substance is released are ascertained. The number and frequency of the administered specimens is subsequently determined according to the amount of bioactive substance that is to be present for a given period of time in the recipient's gastrointestinal system.

It is understood that changes in the available volume offered by the receiving environment do not change over the time release period to an extent such as to materially affect the relationship of direct proportionality between the amount of released active substance and its concentration in the receiving environment. Consequently, the foregoing discussion employs the terms "concentration" and "amount" as applied to the released active substance in the sense that an increase in the amount implies an increase in concentration and, conversely, a decrease in the amount implies a decrease in concentration.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A sustained release composition suitable for use as an excipient for mixing within an orally administered specimen containing a glucosamine-based bioactive substance that can irritate the stomach in order to provide a sustained release of the glucosamine-based bioactive substance and protect the stomach of a user, comprising:

(a) powdered cellulose; and
(b) maltodextrin,
wherein the ratio by weight of the amount of powdered cellulose to the amount of maltodextrin in the sustained release composition is in a range of about 1:9 to about 2:3 such that the amount by weight of the maltodextrin is at least about one and one-half times that of the powdered cellulose, and
wherein, after mixing the sustained release composition with a glucosamine-based bioactive substance in an orally administered specimen in an amount so that the powdered cellulose has a concentration in a range from about 4% to about 14% by weight of the orally administered specimen, the powdered cellulose and the maltodextrin act to slow the disintegration of the orally administered specimen to provide a sustained release of the glucosamine-based or other bioactive substance over a period of time in a range of about one hour to about three hours and form a protective gel in order to reduce or eliminate detrimental side effects on the gastrointestinal system of the glucosamine-based bioactive substance, break-down products of the glucosamine-based bioactive substance, and/or reaction products of the glucosamine-based bioactive substance as the specimen breaks down after ingestion by a user.

2. A sustained release composition as recited in claim 1, wherein the sustained release composition is suitable for reducing stomach irritation by an orally administered specimen that further comprises a chondroitin-based compound.

3. A sustained release composition as recited in claim 1, wherein the sustained release composition is suitable for reducing stomach irritation by an orally administered specimen that further comprises methylsulfonyl methane.

4. A sustained release composition as recited in claim 1, wherein the sustained release composition is suitable for reducing stomach irritation by an orally administered specimen that further comprises a compound selected from the group consisting of glucosamine sulfate, glucosamine hydrochloride, and mixtures thereof.

5. A sustained release composition as recited in claim 1, wherein the sustained release composition is suitable for reducing stomach irritation by an orally administered specimen that further comprises chondroitin sulfate.

6. A sustained release composition as recited in claim 1, wherein the ratio by weight of the amount of powdered cellulose to the amount of maltodextrin in the sustained release composition is in a range of about 1:4 to about 3:7 such that the amount by weight of the maltodextrin is at least about two and one-third times that of the powdered cellulose.

7. A sustained release composition as recited in claim 1, wherein the sustained release composition is suitable for use within an orally administered specimen that is a tablet.

8. A sustained release composition as recited in claim 1, wherein said powdered cellulose has a degree of polymerization in a range of about 440 to about 2250.

9. A sustained release composition as recited in claim 1, wherein said powdered cellulose has a degree of polymerization of about 1432.

10. A sustained release composition as recited in claim 1, wherein said maltodextrin comprises at least one maltodextrin selected from the group consisting of M580 maltodextrin, M700 maltodextrin, and mixtures thereof.

11. A sustained release composition as recited in claim 1, wherein said maltodextrin comprises M510 maltodextrin that is substantially free of wheat protein, barley protein, oat protein, and rye protein.

12. A method for providing sustained release of a glucosamine-based bioactive substance during a chosen time interval, comprising:
(a) providing a delivery specimen comprised of the sustained release composition as recited in claim 1 mixed within the delivery specimen together with a glucosamine-based bioactive substance;
(b) determining the sustained release of the bioactive substance as a function of time to ascertain the effective amount of bioactive substance that is released and to ascertain the time during which said bioactive substance is released; and
(c) determining a delivery specimen intake frequency and a number of said delivery specimens taken to maintain a desired amount of bioactive substance during a chosen time interval.

13. A method as recited in claim 12, wherein said determining the sustained release of the glucosamine-based bioactive substance as a function of time comprises determining the cumulative release of the glucosamine-based bioactive substance as a function of time.

14. A method as recited in claim 12, wherein said determining the sustained release of the glucosamine-based bioactive substance as a function of time comprises determining the incremental release of the glucosamine-based bioactive substance as a function of time.

15. A method as recited in claim 12, wherein said glucosamine-based bioactive substance is a compound selected from the group consisting of glucosamine sulfate, glucosamine hydrochloride, and mixtures thereof.

16. A method as recited in claim 12, wherein said delivery specimen is a tablet.

17. A sustained release orally administered specimen, comprising:
(a) an excipient portion that includes a sustained release composition mixed throughout the orally administered specimen, the sustained release composition comprising:
powdered cellulose included in an amount in a range of about 4% to about 14% by weight of the orally administered specimen; and
maltodextrin in an amount such that the ratio by weight of the amount of powdered cellulose to the amount of maltodextrin in the orally administered specimen is at least about 1:9 with the proviso that the amount of maltodextrin exceeds the amount of powdered cellulose; and
(b) a glucosamine-based bioactive substance mixed with the sustained release composition throughout the orally administered specimen such that the maltodextrin and the cellulose slowly disintegrate when exposed to an aqueous medium to thereby provide a sustained release of the glucosamine-based bioactive substance over a time period in a range of about one hour to about three hours;
wherein the powdered cellulose and the maltodextrin are mixed with the glucosamine-based bioactive substance throughout the orally administered specimen such that, upon ingestion, the sustained release composition forms a protective gel to prevent direct contact between at least a portion of the glucosamine-based bioactive substance and a stomach wall and reduce or eliminate detrimental side effects on the gastrointestinal system of the glucosamine-based bioactive substance, breakdown products of the glucosamine-based bioactive substance, and/or reaction products of the glucosamine-based bioactive substance as the specimen breaks down.

18. A sustained release orally administered specimen as recited in claim 17, wherein said time period is in a range of about one hour to about two hours.

19. A sustained release orally administered specimen as recited in claim 17, wherein said glucosamine-based bioactive substance further comprises a chondroitin-based compound.

20. A sustained release orally administered specimen as recited in claim 17, wherein said glucosamine-based bioactive substance comprises at least one substance selected from the group consisting of glucosamine sulfate, glucosamine hydrochloride, and mixtures thereof.

21. A sustained release orally administered specimen as recited in claim 17, wherein said glucosamine-based bioactive substance further comprises chondroitin sulfate.

22. A sustained release orally administered specimen as recited in claim 17, wherein said glucosamine-based bioactive substance further comprises methylsulfonyl methane.

23. A sustained release orally administered specimen as recited in claim 17, wherein said powered cellulose is included in an amount by weight in the orally administered specimen in a range of about 5% to about 13%.

24. A sustained release orally administered specimen as recited in claim 17, wherein said cumulative sustained release of the glucosamine-based bioactive substance as a function of time increases for a time period of at least about one hour.

25. A sustained release orally administered specimen as recited in claim 17, wherein the incremental sustained release of the glucosamine-based bioactive substance as a function of time provides an amount of the glucosamine-based bioactive substance that is, in any fifty-minute interval during said time period, less than about 50% of the total amount of the glucosamine-based bioactive substance initially present in the orally administered specimen.

26. A sustained release orally administered specimen as recited in claim 17, wherein said orally administered specimen is a tablet.

27. A sustained release orally administered specimen, comprising:
  (a) an excipient portion that includes a sustained release composition mixed throughout the orally administered specimen, the sustained release composition comprising:
    powdered cellulose included in an amount by weight of the orally administered specimen in a range of about 4% to about 14%; and
    maltodextrin in an amount such that the ratio by weight of the amount of powdered cellulose to the amount of maltodextrin in the orally administered specimen is at least about 1:9 with the proviso that the amount of maltodextrin exceeds the amount of powdered cellulose; and
  (b) a glucosamine-based bioactive substance mixed with the sustained release composition throughout the orally administered specimen such that the maltodextrin and the cellulose slowly disintegrate of the orally administered specimen and thereby provide in an aqueous medium a sustained release of the glucosamine-based substance for a time interval in a range of about one hour to about three hours, such that the released glucosamine-based substance does not significantly irritate a recipient's stomach lining as the specimen breaks down in the stomach;
  wherein the powdered cellulose and the maltodextrin are mixed with the glucosamine-based substance throughout the orally administered specimen such that, upon ingestion, the sustained release composition gels forms a protective gel to prevent direct contact between at least a portion of the glucosamine-based substance and a stomach wall and thereby act as a stomach guard with respect to the glucosamine-based substance as the specimen breaks down in the stomach.

28. A sustained release orally administered specimen as recited in claim 27, wherein said maltodextrin is a commercial maltodextrin free from wheat protein, barley protein, oat protein, and rye protein.

29. A sustained release orally administered specimen as recited in claim 27, wherein said specimen is a tablet.

30. A sustained release orally administered specimen as recited in claim 27, wherein said powdered cellulose is included in an amount by weight in the orally administered specimen in a range of about 5% to about 13%.

31. A sustained release orally administered specimen as recited in claim 27, wherein the ratio by weight of the amount of powdered cellulose to the amount of maltodextrin in the orally administered specimen is in a range of about 1:9 to about 2:3 such that the amount by weight of the maltodextrin is at least one and one-half times that of the powdered cellulose.

32. A sustained release orally administered specimen as recited in claim 27, wherein the ratio by weight of the amount of powdered cellulose to the amount of maltodextrin in the orally administered specimen is in a range of about 1:4 to about 3:7 such that the amount by weight of the maltodextrin is at least about two and one-third times that of the powdered cellulose.

33. A method for providing sustained release of a bioactive substance during a chosen time interval, comprising:
  (a) providing a sustained release orally administered specimen as recited in claim 20;
  (b) determining the sustained release of the bioactive substance as a function of time to ascertain the effective amount of bioactive substance that is released and to ascertain the time during which said bioactive substance is released; and
  (c) determining an intake frequency and a number of said delivery specimens to maintain a desired amount of bioactive substance during a chosen time interval.

34. A method as recited in claim 33, wherein said determining the sustained release of the bioactive substance as a function of time comprises determining at least one of the cumulative release of the bioactive substance as a function of time and the incremental release of the bioactive substance as a function of time.

35. A method as recited in claim 33, wherein said maltodextrin comprises at least one maltodextrin selected from the group M510 maltodextrin, M580 maltodextrin, M700 maltodextrin, and mixtures thereof.

36. A method as recited in claim 33, wherein the powdered cellulose is included in an amount by weight in the delivery specimen in a range of about 5% to about 13%.

37. A method as recited in claim 33, wherein the delivery specimen is a tablet, and the ratio by weight of the amount of powdered cellulose to the amount of maltodextrin in the delivery specimen is in a range of about 1:4 to about 3:7 such that the amount by weight of the maltodextrin is at least about two and one-third times that of the powdered cellulose.

* * * * *

UNITED STATES PATENT AND TRADEMARK OFFICE
CERTIFICATE OF CORRECTION

| | | |
|---|---|---|
| PATENT NO. | : 7,056,531 B1 | Page 1 of 1 |
| APPLICATION NO. | : 09/849611 | |
| DATED | : June 6, 2006 | |
| INVENTOR(S) | : Swenson et al. | |

It is certified that error appears in the above-identified patent and that said Letters Patent is hereby corrected as shown below:

Column 4
Line 19, change "it not" to --it is not--

Signed and Sealed this

Eleventh Day of May, 2010

David J. Kappos
*Director of the United States Patent and Trademark Office*